United States Patent [19]

Calvo et al.

[11] Patent Number: 4,466,955
[45] Date of Patent: Aug. 21, 1984

[54] SKIN BLEACHING STICK CONTAINING HYDROQUINONE

[75] Inventors: Luis C. Calvo, Bayshore; Irene C. Obernier, Northport; Steve J. Hasher, Holbrook, all of N.Y.

[73] Assignee: Germaine Monteil Cosmetiques Corporation, Deer Park, N.Y.

[21] Appl. No.: 386,820

[22] Filed: Jun. 9, 1982

[51] Int. Cl.$^3$ .................. A61K 7/135; A61K 7/44
[52] U.S. Cl. .................. 424/62; 424/DIG. 5; 424/59; 424/60
[58] Field of Search .................. 424/62, DIG. 5, 59, 424/60

[56] References Cited

U.S. PATENT DOCUMENTS

| | | | |
|---|---|---|---|
| 2,376,884 | 4/1945 | Schwenk et al. | 424/59 |
| 2,377,188 | 5/1945 | Schwenk et al. | 424/59 |
| 2,566,722 | 9/1951 | Friedberg | 424/DIG. 5 |
| 2,965,678 | 12/1960 | Sundberg et al. | 424/341 X |
| 3,856,934 | 12/1974 | Kligman | 424/62 |
| 4,136,166 | 1/1979 | Barnett et al. | 424/62 |
| 4,239,781 | 12/1980 | Edwards | 424/DIG. 5 |

FOREIGN PATENT DOCUMENTS 0053611 5/1981 Japan .................. 424/DIG. 5

OTHER PUBLICATIONS

Brown, A New Cosmetic Fluid Emollient, 12/6/1979, pp. 1 to 4.

*Primary Examiner*—Dale R. Ore
*Attorney, Agent, or Firm*—Wolder, Gross & Yavner

[57] ABSTRACT

This invention relates to skin bleaching compositions for localized application based on hydroquinone in anhydrous cosmetic formulations.

8 Claims, No Drawings

SKIN BLEACHING STICK CONTAINING HYDROQUINONE

FIELD OF THE INVENTION

This invention relates to skin-lightening cosmetics and methods for lightening hypermelanized skin blemishes "Brown Spots", "Age Spots", and "Liver Spots". More particularly this invention relates to cosmetic compositions for localized application based on hydroquinone in anhydrous cosmetic formulation as the tyrosine-inhibiting melanizing agent.

BACKGROUND OF THE INVENTION

A recent article (S. S. Bleehen: J. Soc. Cosmet. Chem 28 407–412, 1977) aptly stated "Hyperpigmentation of the skin in man can be the cause of much mental distress and hypermelanotic areas, particularly on the face, can result in marked cosmetic disability." While the statement is made in the context of men, it is even more appropriate with regard to women, who, in addition to non-sex-related melanotic blemishes, are also subject to hypermelanotic chloasmas as a result of child-bearing (chloasma gravidarum) and birth-control pills (chloasma pillularae). The prime cosmetic solution to those conditions has been the application of "bleaching" lotions and creams to affected areas.

These lotions and creams are emulsions (W/O or O/W) wherein 1 to 5 wt.% of hydroquinone is dissolved in the aqueous phase. Due to the liquid or semi-liquid nature of the vehicle the hydroquinone is generally distributed over the widely affected areas of the body.

To be effective, the hydroquinone must be absorbed into the lower layers of the skin, in order to inhibit, at the melanocytes, the formation of the enzyme tyrosinase. This enzyme converts the amino-acid tyrosine into melanin, the coloring pigment of the blemish. The use of hydroquinone via aqueous emulsified vehicles is well-known, as seen in U.S. Pat. No. 3,856,934 which describes the combination of hydroquinone with corticosteroids and the keratolytic agent, Vitamin A acid.

This patent and the above mentioned article include an excellent review of the literature of cosmetic lightening (bleaching) of the skin. It is generally recognized that hydroquinone is the least irritating of the tyrosine-inhibiting agents including ammoniated mercury, 4-isopropyl catechol(4-IPC), and hydroquinone monobenzyl ether. Problems with these other agents are their systemic effects. Mercury salts, of course have recognized toxic effects. However the hydroquinone monobenzyl ether and 4-IPC have broad systemic depigmenting effects due to their melanocytotoxic effects. Hydroquinone is the least irritating and has the least amount of systemic effects.

All prior cosmetic preparations containing hydroquinone have been based upon its cream or lotion application due to the solubility limitations imposed by hydroquinone which required the use of water as the solvent. Hydroquinone is soluble in water in a 1:14 ratio. This solution is then the aqueous phase component of the creams and lotions. However aqueous solutions of hydroquinone have finite stability which limits the shelf-life of these previous cosmetic preparations.

In the treatment of skin spots, particularly "Age Spots" "Pill Spots" and "Liver Spots", it would be most desireable to localize the application of the hydroquinone. Application from a solid stick would be most desireable for circumscribed application to the spots or blemishes.

Alcoholic-gel cosmetic sticks of the type popularly used in stick deodorants would appear to be a good base for such cosmetic bleaching sticks since hydroquinone is quite soluble in alcohol. However, the gelling agents in such sticks is sodium stearate, a soap, but the alkalinity of soaps readily and rapidly decomposes hydroquinone. For this reason hydroquinone "bleaching" sticks have not heretofore appeared on the market.

THE INVENTION

It is an object of this invention to provide hydroquinone blemish-bleaching anhydrous formulations for localized topical application.

It is another object of this invention to provide hydroquinone in a form whereby, due to its controlled release into the aqueous cell and tissue fluids from anhydrous topical media, will provide the least amount of adverse effects.

It is another object of this invention to provide hydroquinone cosmetic sticks which have satisfactory, stable shelf life suitable for commercial purposes.

These and other objects are achieved by dissolving melanin-inhibiting amounts of hydroquinone in polypropoxylated or polyethoxylated fatty ethers and incorporating this anhydrous solution into an extended oil and wax non-aqueous cosmetic base.

In such an anhydrous oil-wax base the hydroquinone is more stable and less prone to oxidation since oxygen is less soluble in waxes than in water. The oxygen from the air does not reach the ether and wax-dissolved hydroquinone as readily as if it were solubilized in water. Consequently the stability, potency and shelf-life of the product is maintained over longer periods of time.

Further, these specific polyalkoxylated fatty ethers, which are solubilizing agents for the hydroquinone, are recognized as cosmetic skin-penetrating agents. Being solubilized in such penetrating "oils", the hydroquinone will reach the inner skin layers, where the tyrosinase and melanin are found, for direct, much faster and more localized action than with aqueous solutions of hydroquinone. The polyalkoxylated fatty ethers with the dissolved hydroquinone go through the skin's lipid barrier without difficulty for controlled release of the active form of the hydroquinone.

Once inside the skin, these non-aqueous fatty ethers release the dissolved hydroquinone to the aqueous phase of the surrounding tissue colloids at a slow rate of diffusion. This slow diffusion to the cellular fluids has two advantages. It maintains effective local amounts of hydroquinone at the desired hyper-melanized areas. It also maintains proper, low, effective levels of hydroquinone so that its chemical redox action is much less harsh and less prone to cause irritation and sensitization than if it were administered from highly diffusible aqueous vehicles.

The restriction to, and control of the areas to be "bleached" and the control of the rate of lightening of the blemishes is very important from cosmetic considerations.

The blemishes, particularly the post-pregnancy and birth-control pill chloasmas are not confined to blond, brunette or red-haired Caucasians but are also common among non-Causasian stock. Cosmetically, an evening or blending of skin tone between the blemished and unblemished areas is to be desired. With creams and lotions, by their very physical nature and mode of application, the lightening action is spread generally beyond the blemished areas and often in darker skinned women produces mottled effects including depigmented vitiglio-like areas. With the solid sticks of this invention the hydroquinone is locally applied only to the hypermelanized areas. Due to its controlled slow transfer to the cellular fluids and minimal lateral diffusibility in the skin, the hydroquinone is confined at the desired areas to effect bleaching in these hypermelanized areas with minimal lightening effects in normally pigmented areas. The solid nature of the stick permits circumscribed application to the hyperpigmented blemish. In addition, its easy vertical penetration through the surface lipid barrier cooperates to localize the lightening effects to the affected areas.

Since melanin development is promoted by sunlight and more specifically by certain U V-wavelengths thereof, it is useful to incorporate into the stick composition protective amounts of sun-screen agents. Such sun-screen agents, in cosmetically approved grades, are commercially available. Their specific choice and concentration is merely within the art of the formulator and depends upon the degree of the U V-protection desired. The amounts of such sun-screens should be sufficient to provide an SPF level of at least 10 and preferably more than about 15. This screening effect slows down melanin development until the tyrosinase is sufficiently inhibited by the hydroquinone.

Another advantage to the inclusion of sun-screening agents in the stick composition is as a replacement in the bleached areas of the sun-protective action of melanin. With the melaninformation prevented by the action of hydroquinone, unprotected areas are prone to painful sunburn. The sun-screens in the stick provide a replacement protection.

It is also useful to include within the stick formulation suitable opacifiers and pigments to provide touch-up and matching coloration during the lightening action of the bleach stick which takes place slowly over a matter of several days to weeks. Choice of color and pigment is within the skill of the cosmetic colorist.

While the primary thrust of the invention is directed to presentation of a cosmetic stick formulation, the invention is based on the concept of dissolving the hydroquinone in an anhydrous, non-aqueous solvent and presenting such an anhydrous solution in a non-aqueous cosmetic vehicle. While the stick vehicle has been stressed because it lends itself to topical localized application, the invention in its broadest aspects encompasses non-aqueous, or anhydrous cosmetic compositions containing dissolved hydroquinone. Such compositions with hydroquinone dissolved in an anhydrous solvent have not heretofore been achieved. The invention could also be achieved by blending anhydrous components into cream-like consistency to form products very much like the emulsion products currently on the market. Such products could easily be prepared by balancing the choice and proportions of specific "oils" and waxes.

DETAILS OF THE INVENTION

Hydroquinone, as mentioned above, is the preferred lightening agent as it is the safest and most effective of presently used cosmetic bleaches. It has an additional advantage in that its effects are reversible after discontinuance of use. Some of the other melanocytotoxic bleaches are not readily reversible and any overuse, misuse or abuse can cause disfiguring effects at least as cosmetically abhorrent as the original blemish. The concentration of the hydroquinone in the lightening sticks of this invention ranges from 2 to about 10% by weight. Preferable is the range of from about 2 to 5% of hydroquinone. Optimally for Caucasian skin, about 3% hydroquinone has been useful. Lightening of the chloasmas to match the surrounding skin has been effected in about 3 weeks in some cases.

As stated above, hydroquinone is readily soluble in a recently developed class of polyalkoxylated fatty ethers recognized and approved for cosmetic uses.

These ethers have the formula:

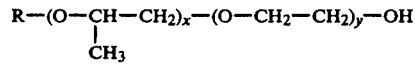

where R is a saturated or unsaturated fatty-alcohol radical or lanolin-alcohol radical and x and y are independently integers of 0 to about 50 with the sum of x and y being at least 2 to about 70. The CTFA Cosmetic Ingredient Dictionary lists many suitable polyalkoxylated fatty ethers.

Where x is a positive integer these ethers are propoxylated. Where y is a positive integer these ethers are ethoxylated. Mixed alkoxy-ethers where x and y are both positive integers are also useful.

The fatty alcohol radicals may have from 9 to 20 carbon atoms in the chain, which chain may be saturated or unsaturated. The commercial fatty, alkoxylated ethers are based on myristyl, cetyl, stearyl. and oleyl fatty alcohol and lanolin alcohol.

These fatty ethers are useful in the composition of this invention in amounts ranging from 30 to 60 weight percent. Smaller amounts are insufficient to satisfactorily dissolve the hydroquinone. Larger amounts are difficult to solidify into stick form. For sticks the amounts are in the range of 40 to 45%. For anhydrous creams greater amounts may be used.

The CTFA Cosmetic Ingredient Dictionary (1981 edition) lists the following commercially available ether we found to be effective for dissolving hydroquinone.

PEG ethers

Oleth 2,3,4,5,10, 15, 20, 23, 25 and 50 are the polyethylene glycol ethers of Oleyl alcohol where the number indicates the moles of ethylene oxide per mole of the fatty ether. Also useful are Polyoxyethylene$_{(x)}$. Oleyl ether Phosphates where x is 4,10 or 20.

PPG ethers

PPG-10 Oleyl ether; PPG-20 Oleyl ether PPG-23 Oleyl ether; PPG-30 Oleyl ether; PPG-50 Oleyl ether; PPG-10 Cetyl ether; PPG-20 Detyl ether; PPG-30 Cetyl ether; PPG-50 Cetyl ether; PPG-15 Stearyl ether; PPG-30 Isocetyl ether; PPG-3 Myristyl ether; PPG-4 Myristyl ether; PPG-2 Lanolin ether; PPG-5 Lanolin ether; PPG-10 Lanolin ether; PPG-20 Lanolin ether; PPG-30 Lanolin ether.

Mixed Alkoxy Ethers

PPG-12 Laneth 50; PPG-3 Myreth-3; PPG-3 Myreth-11.

Other fatty alcohol moieties can be used in these ethers. The choice of specific fatty alcohol moiety and the degree and proportion of alkoxylation is governed by the specific skin absorption speed desired. Too rapid absorption is not desired as this increases horizontal (lateral) diffusion of the hydroquinone too far beyond the localized areas of application. Delaying vertical diffusion slows the lightening action excessively so that melanin is formed more rapidly than its formation can be prevented by penetration of the hydroquinone to the melanocytes where it performs its tyrosine-inhibiting functions.

The anhydrous solution of the hydroquinone in the alkoxylated fatty ether is preferably extended with a fatty alcohol ($C_9$ to $C_{19}$) or an oil containing an alcohol (—OH) group such as castor oil. These fatty alcohols are listed in the CTFA Cosmetic Ingredient Dictionary. The presence of the alcohol function promotes a coupling action between the fatty portion of the extender molecule and the hydroquinone solution. This permits extension of the solubility of hydroquinone into oils and the waxes used as cosmetic creams or for solid stick bases.

The aforementioned waxes play the role of anhydrous consistency providers to maintain the vehicle consistency particularly the integrity of the stick. Substantially anhydrous vegetable waxes, hydrocarbon waxes, mineral and synthetic waxes are all suitable provided they give a stick with satisfactory consistancy and acceptable hydroquinone-compatible cosmetic characteristics. To the waxes may be added suitable non-aqueous plasticizers to impart plasticity and elasticity and provide cosmetic elegance.

Once the non-aqueous hydroquinone solution has been effected and extended at room temperature to form sticks, it can be added to a secondary blend containing melted waxes and fatty alcohols. The entire anhydrous mixture should then be molded and immediately cooled.

The rapid cooling is necessary as hydroquinone decomposes readily with heat. If cooling is rapidly performed, the anhydrous bleaching sticks, upon unmolding, are beautifully formed with very appealing cosmetic characteristics.

In general when preparing the anhydrous formulation of this invention, the alkoxylated fatty ether is introduced into a covered vessel fitted with a heating jacket, a slow speed mixer and a source of nitrogen as a purging gas. The fatty ether is warmed to about 45° C. and the hydroquinone is added. Heating is discontinued. The nitrogen purge is started and mixing is continued until all the hydroquinone is dissolved. The fatty alcohol extender is then added with continued mixing until the temperature drops.

In a separate vessel all the other oils and waxes are heated. Once melted, the temperature of the mixture is brought to 65° C. and maintained at that temperature with slow agitation.

The mixture containing the non-aqueous solution of hydroquinone is added to the warm waxes in the quantity sufficient to fill the mold. This mixture is rapidly poured into the mold. The mold is placed on a refrigerated table and cooled until solidified. The sticks are removed from the mold and inserted into cases.

The above procedures were followed in preparing cosmetic lightening "bleach sticks" of the following examples. The formulae of these examples illustrate the range of the invention. The examples all formed satisfactory anhydrous cosmetic sticks that effectively lightened hyperpigmented skin areas to which the formulations were repeatedly applied.

EXAMPLES

Manufacturing Procedure for Hydroquinone-containing Sticks (A) Melt all oils and waxes, except Oleyl Alcohol, the fatty ether and Hydroquinone. This should be done in a steam jacketed Stainless Steel kettle. Once melted, bring temperature to 65° C. and hold at that temperature under slow agitation.

(B) In a separate container, provided with a slow speed mixer, add the fatty ether and warm to 45° C. Then add Hydroquinone, cover the vessel and inject a low flow of Nitrogen so as to displace air from the space above the surface of the ether-Hydroquinone blend. Continue mixing until all Hydroquinone is dissolved, then add formula amount of Oleyl Alcohol. Continue mixing and let temperature drop. Do not add additional heat.

(C) Add (B) to (A) under slow mixing in the quantity sufficient to fill one mold at a time. Pour immediately into the mold. Place on refrigerated table and let cool until completely solidified. Remove sticks from mold and insert in cases.

EXAMPLE 1

| Isopropyl Lanolate | 7.000 |
|---|---|
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-3 Myristyl Ether | 41.200 |
| Hydroquinone | 4.000 |
| | 100.000% |

EXAMPLE 2

| Shea Butter Unsaponifiables | 3.000 |
|---|---|
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-3 Myristyl Ether | 43.200 |
| | 100.000% |

EXAMPLE 3

| Isopropyl Lanolate | 7.000 |
|---|---|
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-4 Myristyl Ether | 41.200 |
| Hydroquinone | 4.000 |
| | 100.000% |

EXAMPLE 4

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-4 Myristyl Ether | 43.200 |
| | 100.000% |

EXAMPLE 5

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-30 Iso Cetyl Ether | 41.200 |
| Hydroquinone | 4.000 |
| | 100.000% |

EXAMPLE 6

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Caster Oil | 3.000 |
| Hydroquinone | 2.000 |
| PPG-30 Iso Cetyl Ether | 42.200 |
| | 100.000% |

EXAMPLE 7

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-30 Oleyl Ether | 41.200 |
| Hydroquinone | 4.000 |
| | 100.000% |

EXAMPLE 8

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |

-continued

| | |
|---|---|
| Butyl Paraben | 0.150 |
| Castor Oil | 3.000 |
| Hydroquinone | 2.000 |
| PPG-30 Oleyl Ether | 43.200 |
| | 100.000% |

EXAMPLE 9

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-30 Cetyl Ether | 41.200 |
| Hydroquinone | 4.000 |
| | 100.000% |

EXAMPLE 10

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-30 Cetyl Ether | 43.200 |
| | 100.000% |

EXAMPLE 11

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-30 Lanolin Ether | 41.200 |
| Hydroquinone | 4.000 |
| | 100.000% |

EXAMPLE 12

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-30 Lanolin Ether | 43.200 |
| | 100.000% |

EXAMPLE 13

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| Oleth 15 | 43.200 |
| | 100.000% |

EXAMPLE 14

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| Oleth 10 | 43.200 |
| | 100.000% |

EXAMPLE 15

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| Oleth 23 | 43.200 |
| | 100.000% |

EXAMPLE 16

| | |
|---|---|
| Isopropyl Lanolate | 14.00 |
| Beeswax | 4.70 |
| Candelilla Wax | 7.10 |
| Ozokerite Wax | 13.40 |
| Propyl Parasept | 0.10 |
| Talc | 18.00 |
| Titanium Dioxide | 1.00 |
| Octyl Dimethyl Paba | 3.00 |
| Benzophenone-3 | 2.00 |
| PPG-3 Myristyl Ether | 31.35 |
| Hydroquinone | 2.00 |
| Oleyl Alcohol | 2.80 |
| Allantoin Urocanate | 0.15 |
| Histidine | 0.05 |
| Fragrance | 0.25 |
| | 100.00% |

We claim:

1. An anhydrous cosmetic blemish-bleaching solid stick composition comprising as the active ingredient an anhydrous solution consisting essentially of a tyrosine-inhibiting amount, in the range 2–10 wt. % of hydroquinone, and 40 to 45 wt.% of an alkoxylated fatty ether of the formula $$R-(O-CH(CH_3)-CH_2)_x-(O-CH_2-CH_2)_y-OH$$

where R is a saturated or unsaturated fatty alcohol radical or lanolin alcohol radical and x and y are independent integers of 0 to about 50, with the sum of x and y ranging from at least 2 to about 70 and a non-aqueous cosmetically acceptable vehicle selected from the group consisting of fatty alcohol, oil containing an alcohol group, fat and wax.

2. The composition according to claim 1 having the formula

| | | wt. % |
|---|---|---|
| Hydroquinone | | 2–5 |
| Alkoxylated Fatty Ether | | 40–45 |
| Anhydrous Stick Forming Vehicle | to | 100%. |

3. The composition according to claim 1 having essentially the formula

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-3 Myristyl Ether | 43.200 |
| | 100.000% |

4. The composition according to claim 1 having essentially the formula

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-4 Myristyl Ether | 41.200 |
| Hydroquinone | 4.000 |
| | 100.000% |

5. The composition according to claim 1 having essentially the formula

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Caster Oil | 3.000 |
| Hydroquinone | 2.000 |
| PPG-30 Iso Cetyl Ether | 42.200 |
| | 100.000% |

6. The composition according to claim 1 having essentially the formula

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| PPG-30 Oleyl Ether | 43.200 |
| | 100.000% |

7. The composition according to claim 1 having essentially the formula

| | |
|---|---|
| Isopropyl Lanolate | 7.000 |
| Shea Butter | 3.000 |
| Oleyl Alcohol | 9.700 |
| Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| PPG-30 Lanolin Ether | 41.200 |
| Hydroquinone | 4.000 |
| | 100.000% |

8. The composition according to claim 1 having essentially the formula

| | |
|---|---|
| Shea Butter Unsaponifiables | 3.000 |
| Isopropyl Lanolate | 7.000 |
| Oleyl Alcohol | 9.700 |
| White Beeswax | 13.500 |
| Esbesco Wax | 13.500 |
| Ozokerite | 4.800 |
| Propyl Paraben | 0.150 |
| Butyl Paraben | 0.150 |
| Castor Oil | 3.000 |
| Hydroquinone | 2.000 |
| Oleth 10 | 43.200 |
| | 100.000% |

* * * * *